United States Patent

Mariaucue et al.

(10) Patent No.: US 6,765,333 B1
(45) Date of Patent: Jul. 20, 2004

(54) POWER ASSISTANCE DEVICE FOR AN ULTRASONIC VIBRATION DENTAL HANDPIECE

(75) Inventors: Dominique Mariaucue, Le Haillan (FR); Xavier Capet, Cestat Gazinet (FR); Pascal Cabrignac, Merignac (FR)

(73) Assignee: Satelec SA, Merignac (FR)

( * ) Notice: Subject to any disclaimer, the term of this patent is extended or adjusted under 35 U.S.C. 154(b) by 47 days.

(21) Appl. No.: 10/019,527

(22) PCT Filed: Jul. 5, 2000

(86) PCT No.: PCT/FR00/01932

§ 371 (c)(1),
(2), (4) Date: Apr. 2, 2002

(87) PCT Pub. No.: WO01/01878

PCT Pub. Date: Nov. 1, 2001

(30) Foreign Application Priority Data

Jul. 5, 1999 (FR) .............................. 99 08643

(51) Int. Cl.[7] .......................... H01L 41/08; A61B 19/00; H02N 2/00
(52) U.S. Cl. .................. 310/316.01; 310/317; 310/325
(58) Field of Search ............................ 310/316.01, 317, 310/325; 318/114, 116; 388/937

(56) References Cited

U.S. PATENT DOCUMENTS

| | | | |
|---|---|---|---|
| 4,168,447 A | 9/1979 | Bussiere et al. ....... | 310/316.01 |
| 4,242,911 A * | 1/1981 | Martin ................... | 73/620 |
| 4,308,229 A * | 12/1981 | Voit ....................... | 422/20 |
| 4,371,816 A | 2/1983 | Wieser ................... | 310/316.01 |
| 4,957,100 A * | 9/1990 | Herzog et al. .......... | 310/317 |
| 5,181,052 A * | 1/1993 | McClellan .............. | 351/156 |
| 5,638,830 A * | 6/1997 | Valade .................... | 128/897 |
| 5,728,130 A * | 3/1998 | Ishikawa et al. ........ | 606/185 |
| 6,136,020 A * | 10/2000 | Faour ..................... | 607/96 |
| 6,436,129 B1 * | 8/2002 | Sharkey et al. ......... | 607/96 |

FOREIGN PATENT DOCUMENTS

| FR | 2 550 440 | 2/1985 | ........... A61C/17/00 |
|---|---|---|---|
| WO | WO 9629023 A1 * | 9/1996 | ........... A61C/17/20 |

* cited by examiner

Primary Examiner—Thomas M. Dougherty
Assistant Examiner—J. Aguirrechea
(74) Attorney, Agent, or Firm—Young & Thompson

(57) ABSTRACT

A power assistance device for an ultrasonic dental handpiece (5) includes a working circuit with a parallel impedance (Ls) between the output terminals (S1,S2) and a control circuit with a current transformer (T2), the primary winding (7) thereof is serially arranged in the working circuit and the secondary winding (11) thereof forms an RLC circuit in conjunction with a capacitor (13) and a resistor (15) associated therewith. The voltage of the circuit at the terminals of the resistor (15) is transmitted to the input of a power supply (1). The control circuit enables variations in the value of the capacitor (13) and/or the value of the self-inductance coil of the secondary winding (11) of the transformer (T2).

17 Claims, 1 Drawing Sheet

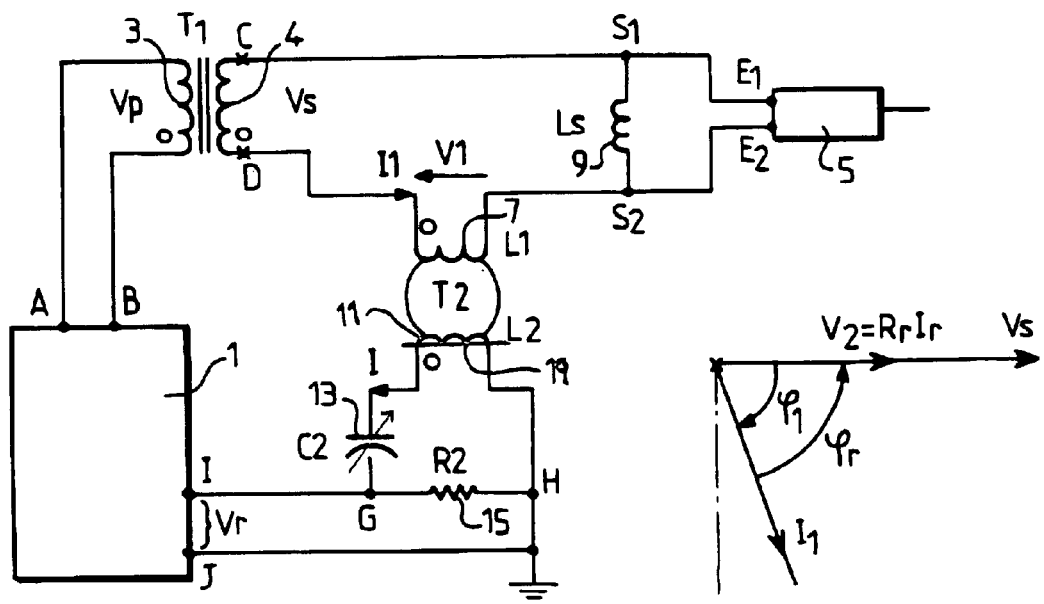
FIG.1
FIG.2
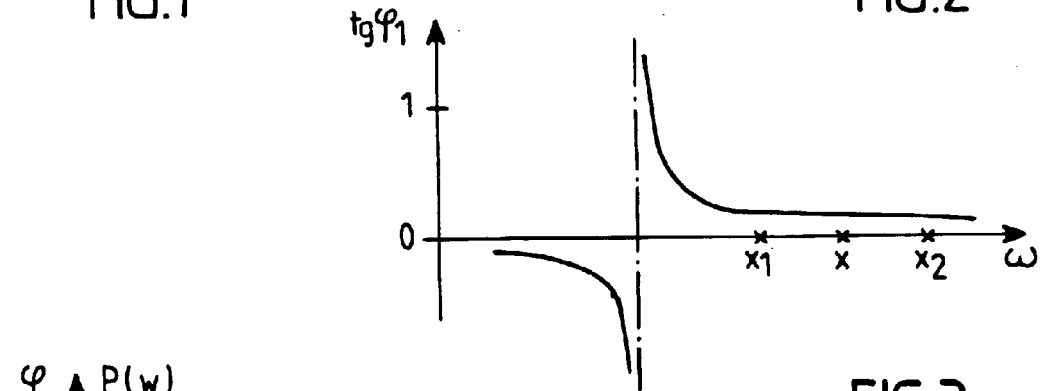
FIG.3
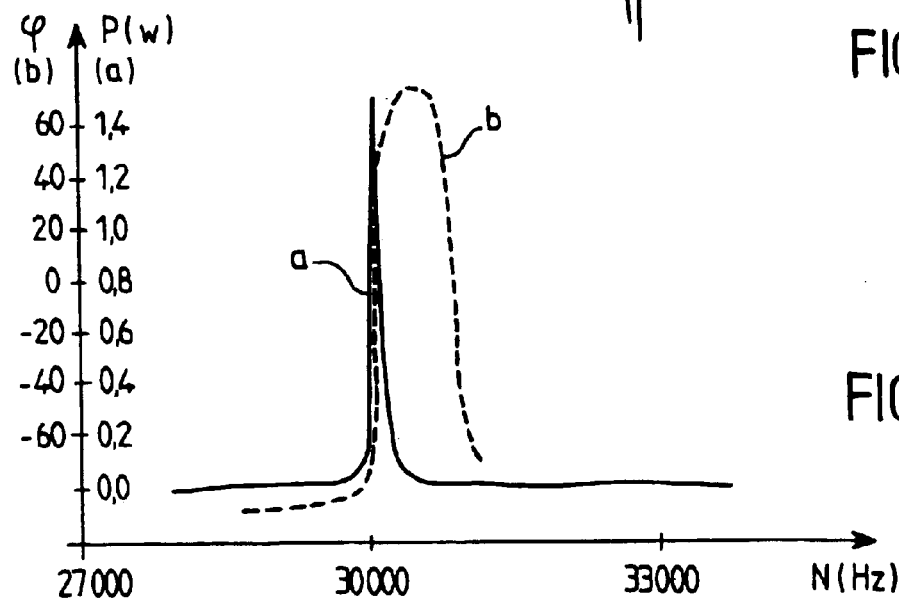
FIG.4

POWER ASSISTANCE DEVICE FOR AN ULTRASONIC VIBRATION DENTAL HANDPIECE

BACKGROUND OF THE INVENTION

The present invention relates to an electronic servo-control device for dental handpiece, of the type in which the vibration of a tool is obtained by means of a piezoelectric transducer.

DESCRIPTION OF THE RELATED ART

It is known that a piezoelectric transducer generating ultrasound vibrations is, where possible, used in resonance so as to obtain maximum amplitudes and power of the vibrations. When such a transducer, to which a tool is mechanically coupled, comes into contact during a work phase with tissues of different natures, i.e. hard tissues, soft tissues, with or without the presence of a liquid, its resonant circuit evolves during the work. It is known that, in such a handpiece, the speed of vibration of the transducer is a direct function of the electric current which circulates therein and that the effort necessary for this vibration is a direct function of the supply voltage at the terminals of said transducer. It will be understood that, if it is desired that a handpiece operates with optimum yield, the vibrations of the transducer must correspond to the series resonance of this handpiece and, during work, the operational conditions must vary so as to remain in resonance.

SUMMARY OF THE INVENTION

According to the invention, the frequency will be tracked by observing the phase-shift which exists between the voltage and the current supplied and by electrically compensating the intrinsic capacity of the transducer. Such an electric circuit is translated in series resonance by a low impedance and a zero phase-shift.

The present invention thus has for its object to propose such a device for servo-control of the piezoelectric transducer of a vibration generator for dental handpiece, adapted to operate permanently at series resonance frequency, whatever the nature of the tissues on which the tool with which this handpiece is equipped, operates.

The present invention thus relates to a device for servo-control of a dental handpiece activated by an ultrasound generator, comprising supply means of given frequency, characterized in that:

it comprises two circuits, namely a work circuit to whose terminals the ultrasound generator is connected, and a control circuit, the work circuit comprises an inductance in parallel between its output terminals, the supply is adapted to deliver at the output a voltage in phase with a voltage which is delivered thereto on its input, the control circuit is constituted by an intensity transformer whose primary is arranged in series in the work circuit and whose secondary forms, with a capacitor and a resistor associated therewith, an RLC circuit of which the voltage at the terminals of the resistor is sent to the input of said supply, the control circuit comprises means for varying the value of the capacitor and/or that of the self-induction coil of the secondary of the intensity transformer.

The secondary of the intensity transformer preferably comprises a core mobile inside its winding adapted to vary its inductance.

In a preferred embodiment, the supply means will be connected to the work circuit via a voltage transformer of which the inductances of the primary and of the secondary will be high.

In an interesting form of embodiment of the invention, the inductance arranged between the output terminals of the work circuit will be such that, with the intrinsic capacitance of the handpiece and the internal resistance thereof, an RLC circuit close to the resonance is formed.

BRIEF DESCRIPTION OF THE DRAWINGS

A form of embodiment of the present invention will be described hereinafter by way of non-limiting example, with reference to the accompanying drawings, in which:

FIG. 1 schematically shows a frequency tracking device according to the invention.

FIG. 2 schematically shows the phase-shifts between current and intensity in a circuit of the type shown in FIG. 1.

FIG. 3 is a curve representing the variation of the phase-shift between current and voltage in a circuit according to the invention as a function of a multiple of the frequency.

FIG. 4 is a curve representing the respective variations as a function of the frequency, of the power supplied to a specific handpiece and of the corresponding phase-shift between current and intensity.

DESCRIPTION OF THE PREFERRED EMBODIMENT

The frequency tracking oscillator shown in FIG. 1 is essentially constituted by a supply 1 capable of generating between its two output terminals A and B a voltage $V_P$ which supplies the primary 3 of a voltage transformer $T_1$. One of the terminals C of the secondary 4 of this transformer is connected to an output S1 of the circuit to which an input $E_1$ of a handpiece 5 is connected. The other terminal D of this same secondary 4 is connected to the other output S2 of the circuit with the interposition of the primary 7 of a current transformer $T_2$. The second input E2 of the handpiece 5 is connected to the terminal S2. An inductance 9 of value $L_s$ is arranged in parallel between the input terminals $E_1$ and $E_2$ of the handpiece 5.

As is shown in FIG. 1, the secondary 11 of the intensity transformer $T_2$ is arranged in series with a capacitor 13 of value $C_2$ and a resistor 15 of value $R_2$, the latter representing the parasitic resistors of the RLC circuit thus formed.

The terminals G and H of the resistor 15 are connected to input terminals IJ of the supply 1.

There are thus two circuits, namely a work circuit which controls the handpiece 5 and a control circuit constituted by the RLC circuit.

The supply 1 is constituted so that the voltage $V_P$ produced on its output terminals A, B is in phase with the voltage $V_r$ existing between its input terminals I and J.

Under these conditions, as schematically shown in FIG. 2, for the oscillator constituted by the self-induction coil 11, the capacitor 13 and the resistor 15 to enter in oscillation, the signal of voltage $V_r$ collected at the terminals of the resistor $R_2$ must be in phase with $V_s$, which condition is met if $\phi 2 = -\phi 1$. In effect, $\phi 2$ and $\phi 1$ represent the phase-shift between voltage and intensity respectively in the oscillating control RLC circuit and in the work circuit controlling the vibrations of the handpiece 5.

If the voltage $V_r$ existing between the input terminals I and J of the supply 1 is expressed as a function of the current $I_1$ circulating in the primary 7 of the transformer T2, it will be noted that the current $I_1$ is delayed by $\phi 1$ with respect to voltage $V_s$ (or to voltage $V_P$) and that the voltage $V_r$ is in phase with the current $I_2$.

If the equations of the transformer are taken into account, the following will be obtained by using the complex mathematical notification:

$$V_1 = Z_1 I_1 + jm\omega I_2 \text{ with } Z_1 = jL_1 \omega \qquad (1)$$

$$0 = Z_2 I_2 + jm\omega I_1 \text{ with } Z_2 = R_2 + j(L_2 \omega - 1/C_2 \omega) \qquad (2)$$

m representing the coefficient of mutual inductance of one of the windings of the transformer on the other winding.

The transformer $T_2$ being an intensity transformer, it is possible, in known manner, to disregard the influence of the secondary winding on the primary winding so that the expression $jm\omega I_2 = 0$ and the value of $I_1$ is drawn from equation (1), viz.:

$$I_1 = V_1/jL_1\omega = -jV_1/L_1\omega$$

By transferring this value in equation (2), the expression of the current $I_1$ in the work circuit as a function of the current $I_2$ in the RLC circuit is obtained, viz.:

$$I_1 = 1/m\omega(1/C_1\omega - L_2\omega + jR_2)I_2$$

Under these conditions, the phase-shift of the current $I_2$ with respect to current $I_1$ will be:

$$tg\phi_2 = R_2/\omega/(1/C_2\omega - L_2\omega) = R_2 C_2 \omega/1 - L_2 C_2 \omega^2 \qquad (3)$$

Under these conditions, as mentioned hereinbefore, there will be oscillation if $\phi_2 = -\phi_1$ or $t_g\phi_2 = -t_g\phi_1$, viz. from the equation (3):

$$R_2 C_2 \omega / 1 - L_2 C_2 \omega^2 = -t_g \phi_1 \qquad (4)$$

FIG. 3 shows the variation of the value of $t_g \phi_1$ as a function of the value of $\omega$ which represents the vibration frequency, to within the value of $2\pi (\omega = 2\pi N)$.

It will be noted that, without handpiece, the load of the oscillator in the work circuit is reduced to the value of the inductance Ls arranged in parallel between the output terminals $S_1$ and $S_2$ of the circuit. Furthermore, if $R_s$ designates the internal resistance of the oscillator, the phase-shift of the current $I_l$ with respect to $V_s$ is expressed by the expression:

$$t_{g\phi} = L_s/R_s$$

The condition of oscillation $tg\phi_2 = -tg\phi_1$ then becomes:

$$R_2 C_2 \omega / (1 - L_2 C_2 \omega^2) = -L_s \omega_s / R_s$$

or $\omega^2 = (L_s + R_s R_2 C_2)/(L_s L_2 C_2) \qquad (5)$

By playing on the values of $L_2$ of the winding of the secondary 11 of the transformer $T_2$ and/or the value $C_2$ of the capacitor 13, the frequency of the oscillator may be adjusted off-load so that the synchronization curve shown in FIG. 3 is modified.

The secondary 11 may include a core 19, the core 19 being mobile within the secondary 11 to vary to its inductance $L_2$.

In practice, $R_2$ represents the parasitic resistances of the circuit and $C_2$ will be conserved constant.

For each apparatus of a given series, it will then suffice to vary the value $L_2$ of the secondary 11 of the transformer $T_2$ until the voltage $T_1$ is in phase with the current $I_1$ circulating in the circuit.

The apparatus will then be calibrated and the oscillator will "lock" on the inductive delay load $L_s$.

Furthermore, as shown in FIG. 4, a curve is available, which represents the variation of the power at the terminals E1, E2 of the handpiece 5, as well as the value of the phase-shift between current and intensity at the terminals thereof. Each type of handpiece 5 provided with a determined tool will thus have a curve of this type.

In the example of FIG. 4, it will be observed that the power is maximum and the phase-shift is zero for a frequency of around 30 kHz. This value plotted at point X in the diagram of FIG. 3 shows that the adjustment of the RLC circuit is correct since the value of $tg\phi_1$ for this frequency is close to 0.

It is, of course, known that, during operation of the handpiece, the value of the frequency for which a maximum vibration with zero phase-shift is obtained, varies as a function, on the one hand, of the physical nature of the handpiece but also as a function of the surface state of the material to be treated. For a handpiece and a given tool, two extreme frequencies $N_1$ and $N_2$ will therefore be obtained, corresponding to the tool working on soft tissues and harder elements, to which values $X_1$ and $X_2$ of $\omega$ will correspond, as shown in FIG. 3.

It has been observed that, in general, the frequency N lay at about 30 kHz. Under these conditions, an off-load adjustment of each circuit produced will be proceeded with (by adjusting the value of $L_2$ for example) so that, during work, points $X_1$ and $X_2$ indeed lie within zones for which $tg_1$ is close to zero, as shown in FIG. 3.

The variation of the inductance $L_2$ may in particular be obtained by displacing a core at the centre of the self-induction coil 11.

What is claimed is:

1. A device for servo-control of a dental handpiece, comprising:
    a supply means (1) with supply output terminals (A, B) and supply input terminals (I, J), the supply input terminals supplied with a supply input voltage (Vr);
    a work circuit supplied by the supply means and with output terminals (S1, S2) connected to input terminals (E1, E2) of a dental handpiece (5) and with a first inductance (Ls) connected in parallel between the output terminals of the work circuit; and
    a control circuit comprising an intensity transformer (T2) with a primary (7) arranged in series with the work circuit and a secondary (11) in series with a capacitor (13) and a resistor (15), the secondary in series with the capacitor and the resistor forming an RLC circuit, terminals of the resistor being connected to the supply input terminals of the supply means so that a voltage at the terminals of the resistor is the supply input voltage, wherein,
    the supply means is adapted to deliver, at the supply output terminals, a supply output voltage (Vs) in phase with the supply input voltage applied at the supply input terminals, and
    one of the capacitor and a self-induction coil of the secondary of the intensity transformer are to providing one of a variable capacitance and a variable inductance.

2. The device of claim 1, wherein the secondary of the intensity transformer comprises a core (19), the core being mobile within a winding of the secondary to vary an inductance of the secondary.

3. The device of claim 1, wherein the work circuit is connected to the supply output terminals via a voltage transformer (T1).

4. The device of claim 1, wherein the first inductance is positioned such that an inductance of the first inductance and an intrinsic capacitance of the handpiece and an internal resistance of the handpiece form an approximately resonant RLC circuit.

5. A servo-control device for a dental handpiece, comprising:
- a supply (1) with supply output terminals (A, B) and supply input terminals (I, J), the supply input terminals supplied with a supply input voltage (Vr);
- a work circuit operatively supplied by the supply and with output terminals (S1, S2) connected to input terminals (E1, E2) of a dental handpiece (5) and with a first inductance (Ls) connected in parallel between the output terminals of the work circuit; and
- a control circuit comprising an intensity transformer (T2) with a primary (7) arranged in series with the work circuit and a secondary (11) in series with a capacitor (13) and a resistor (15), the secondary in series with the capacitor and the resistor forming a first RLC circuit, terminals of the resistor being connected to the supply input terminals of the supply so that a voltage at the terminals of the resistor is connected as the supply input voltage at the supply input terminals, wherein,
  - the supply is adapted to deliver, at the supply output terminals, a supply output voltage (Vs) in phase with the supply input voltage applied at the supply input terminals, and
  - one of the capacitor and a self-induction coil of the secondary of the intensity transformer are variable to providing one of a variable capacitance and a variable inductance.

6. The device of claim 5, wherein the secondary of the intensity transformer comprises a core (19) mobile within a winding of the secondary.

7. The device of claim 6, wherein a voltage transformer (T1) connects the work circuit to the supply output terminals.

8. The device of claim 6, wherein the first inductance is positioned such that an inductance of the first inductance and an intrinsic capacitance of the handpiece and an internal resistance of the handpiece form a second RLC circuit.

9. The device of claim 8, wherein the second RLC circuit is a resonant RLC circuit.

10. The device of claim 5, wherein a voltage transformer (T1) connects the work circuit to the supply output terminals.

11. The device of claim 5, wherein the first inductance is positioned such that an inductance of the first inductance and an intrinsic capacitance of the handpiece and an internal resistance of the handpiece form a second RLC circuit.

12. The device of claim 11, wherein the second RLC circuit is a resonant RLC circuit.

13. A servo-control device, comprising:
- a supply (1) with supply output terminals (A, B) and supply input terminals (I, J), the supply input terminals supplied with a supply input voltage (Vr);
- a work circuit operatively supplied by the supply and with output terminals (S1, S2) connected to input terminals (E1, E2) of a load (5) and with a first inductance (Ls) connected in parallel between the output terminals of the work circuit; and
- a control circuit comprising an intensity transformer (T2) with a primary (7) arranged in series with the work circuit and a secondary (11) in series with a capacitor (13) and a resistor (15), the secondary in series with the capacitor and the resistor forming a first RLC circuit, terminals of the resistor being connected to the supply input terminals of the supply so that a voltage at the terminals of the resistor is connected as the supply input voltage at the supply input terminals, wherein,
  - the supply is adapted to deliver, at the supply output terminals, a supply output voltage (Vs) in phase with the supply input voltage applied at the supply input terminals.

14. The device of claim 13, wherein, one of the capacitor and a self-induction coil of the secondary of the intensity transformer are variable to providing one of a variable capacitance and a variable inductance.

15. The device of claim 14, wherein the secondary of the intensity transformer comprises a core (19) mobile within a winding of the secondary.

16. The device of claim 13, wherein a voltage transformer (T1) connects the work circuit to the supply output terminals.

17. The device of claim 13, wherein the first inductance is positioned such that an inductance of the first inductance and an intrinsic capacitance of the load and an internal resistance of the load form a resonant, second RLC circuit.

* * * * *

UNITED STATES PATENT AND TRADEMARK OFFICE
CERTIFICATE OF CORRECTION

PATENT NO. : 6,765,333 B1
DATED : July 20, 2004
INVENTOR(S) : Mariaulle et al.

It is certified that error appears in the above-identified patent and that said Letters Patent is hereby corrected as shown below:

Title page,
Item [75], Inventor, change "Mariaucue" to -- Mariaulle --.

Signed and Sealed this

Fifteenth Day of March, 2005

JON W. DUDAS
*Director of the United States Patent and Trademark Office*